US009186519B2

(12) United States Patent
Kivi

(10) Patent No.: US 9,186,519 B2
(45) Date of Patent: Nov. 17, 2015

(54) WIRELESS COMMUNICATION WITH AN IMPLANTABLE MEDICAL DEVICE

(75) Inventor: Gary P. Kivi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 981 days.

(21) Appl. No.: 12/695,456

(22) Filed: Jan. 28, 2010

(65) Prior Publication Data

US 2011/0184491 A1 Jul. 28, 2011

(51) Int. Cl.
*A61N 1/08* (2006.01)
*A61N 1/372* (2006.01)

(52) U.S. Cl.
CPC .................................. *A61N 1/37276* (2013.01)

(58) Field of Classification Search
USPC ....................................................... 607/30, 60
See application file for complete search history.

(56) References Cited

U.S. PATENT DOCUMENTS

| 4,197,500 | A | | 4/1980 | Klein et al. | |
|---|---|---|---|---|---|
| 4,592,360 | A | * | 6/1986 | Lesnick | 607/60 |
| 5,733,313 | A | * | 3/1998 | Barreras et al. | 607/33 |
| 5,814,089 | A | * | 9/1998 | Stokes et al. | 607/32 |
| 6,200,265 | B1 | | 3/2001 | Walsh et al. | |
| 7,280,872 | B1 | * | 10/2007 | Mosesov et al. | 607/60 |
| 7,650,185 | B2 | | 1/2010 | Maile et al. | |
| 2002/0045920 | A1 | * | 4/2002 | Thompson | 607/60 |
| 2003/0114897 | A1 | | 6/2003 | Von Arx et al. | |
| 2003/0114898 | A1 | * | 6/2003 | Von Arx et al. | 607/60 |
| 2006/0064134 | A1 | | 3/2006 | Mazar et al. | |
| 2006/0122667 | A1 | * | 6/2006 | Chavan et al. | 607/60 |
| 2007/0049983 | A1 | | 3/2007 | Freeberg | |
| 2007/0250126 | A1 | | 10/2007 | Maile et al. | |
| 2008/0046038 | A1 | | 2/2008 | Hill et al. | |
| 2008/0058900 | A1 | | 3/2008 | Berthelsdorf et al. | |
| 2008/0071328 | A1 | | 3/2008 | Haubrich et al. | |
| 2008/0264431 | A1 | | 10/2008 | Masoud et al. | |
| 2010/0249881 | A1 | | 9/2010 | Corndorf | |

FOREIGN PATENT DOCUMENTS

| WO | WO2006068862 | 6/2006 |
|---|---|---|
| WO | WO2007114743 | 10/2007 |
| WO | 2009120517 A1 | 10/2009 |
| WO | 2009143099 A1 | 11/2009 |

OTHER PUBLICATIONS (PCT/US2011/021230) PCT Notification of Transmittal of the International Search Report and the Written Opinion of the International Searching Authority, Mailed Sep. 1, 2011, 8 pages.

* cited by examiner

*Primary Examiner* — Alyssa M Alter
(74) *Attorney, Agent, or Firm* — Michael J. Ostrom

(57) ABSTRACT

The disclosure relates generally to wireless communication with an implantable medical device. An implantable medical device (IMD) may initiate the establishment of a communication session by sending a wakeup communication to an external device with which the IMD desires to communicate. The external device may operate in low power state (sometimes referred to as a sleep state or a low current state) in which the external device occasionally powers up telemetry circuitry to monitor for the wakeup communication from the IMD. Upon receiving the wakeup communication, the external device transitions from the low power state to a high power state to establish the communication session with the IMD. Operating the external device in the low power state when no communication session is established reduces the amount of power consumed by the external device when no telemetry is occurring, thus enabling the external device to be powered by a battery.

17 Claims, 8 Drawing Sheets

WIRELESS COMMUNICATION WITH AN IMPLANTABLE MEDICAL DEVICE

TECHNICAL FIELD

The disclosure relates generally to wireless communication with an implantable medical device.

BACKGROUND

A wide variety of implantable medical devices (IMDs) that deliver a therapy to or monitor a physiologic or biological condition of a patient, or both, have been clinically implanted or proposed for clinical implantation in patients. An IMD may deliver therapy to and/or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy, or therapy to reduce or eliminate a condition or symptoms of the condition of the patient.

The IMD may exchange communications with another device. The IMD may exchange communications with an external device, such as a programming device or a monitoring device (e.g., either attached to the patient or otherwise located near the patient). The information exchanged may be information related to a condition of the patient, such as physiological signals measured by one or more sensors, or information related to a therapy delivered to the patient. This information may be previously stored or real-time information. The IMD may also receive information from the external device, such as configuration information that may be used to configure a therapy to be provided to the patient.

SUMMARY

The disclosure relates generally to wireless communication with an implantable medical device. An implantable medical device (IMD) may initiate the establishment of a communication session by sending a wakeup communication to an external device with which the IMD desires to communicate. The external device may operate in low power state (sometimes referred to as a sleep state or a low current state) in which the external device occasionally powers up telemetry circuitry to monitor for the wakeup communication from the IMD. Upon receiving the wakeup communication, the external device transitions from the low power state to a high power state to establish the communication session with the IMD. Operating the external device in the low power state when no communication session is established reduces the amount of power consumed by the external device when no telemetry is occurring, thus enabling the external device to be powered by a battery.

In one example, this disclosure is directed to a device comprising an antenna to transmit or receive communications from the medical device and a telemetry module coupled to the antenna. The telemetry module is configured to operate in a low power state in which the telemetry module interleaves intervals during which one or more components of the telemetry module are powered down with intervals during which the one or more components of the telemetry module are powered up. The telemetry module is also configured to receive a wakeup communication from the implantable medical device, transition from the low power state to a high power state in response to receiving the wakeup communication, and transmit one or more communications to the implantable medical device to establish a communication session.

In another example, this disclosure is directed to a method comprising operating a telemetry module of the device in a low power state in which the telemetry module interleaves intervals during which one or more components of the telemetry module are powered down with intervals during which the one or more components of the telemetry module are powered up, receiving a wakeup communication from the implantable medical device, transitioning the telemetry module from the low power state to a high power state in response to receiving the wakeup communication, and transmitting one or more communications from the device to the implantable medical device to establish a communication session.

In a further example, this disclosure is directed to a device comprising an antenna to transmit or receive communications from a second medical device and a telemetry module coupled to the antenna. T telemetry module configured to transmit one or more wakeup communications in accordance with a first communication mode to the second device to transition the second device from a low power state to a high power state in response to detecting an event with the implantable medical device, receiving one or more communications from the second device to establish a communication session, and transmitting one or more communications to the second medical device in accordance with a second communication mode.

In another example, this disclosure is directed to a method comprising detecting an event with an implantable medical device, transmitting one or more wakeup communications in accordance with a first communication mode to a second device with which the implantable medical device desires to communicate to transition the second device from a low power state to a high power state, receiving one or more communications from the second device to establish a communication session, and transmitting one or more communications to the second medical device in accordance with a second communication mode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
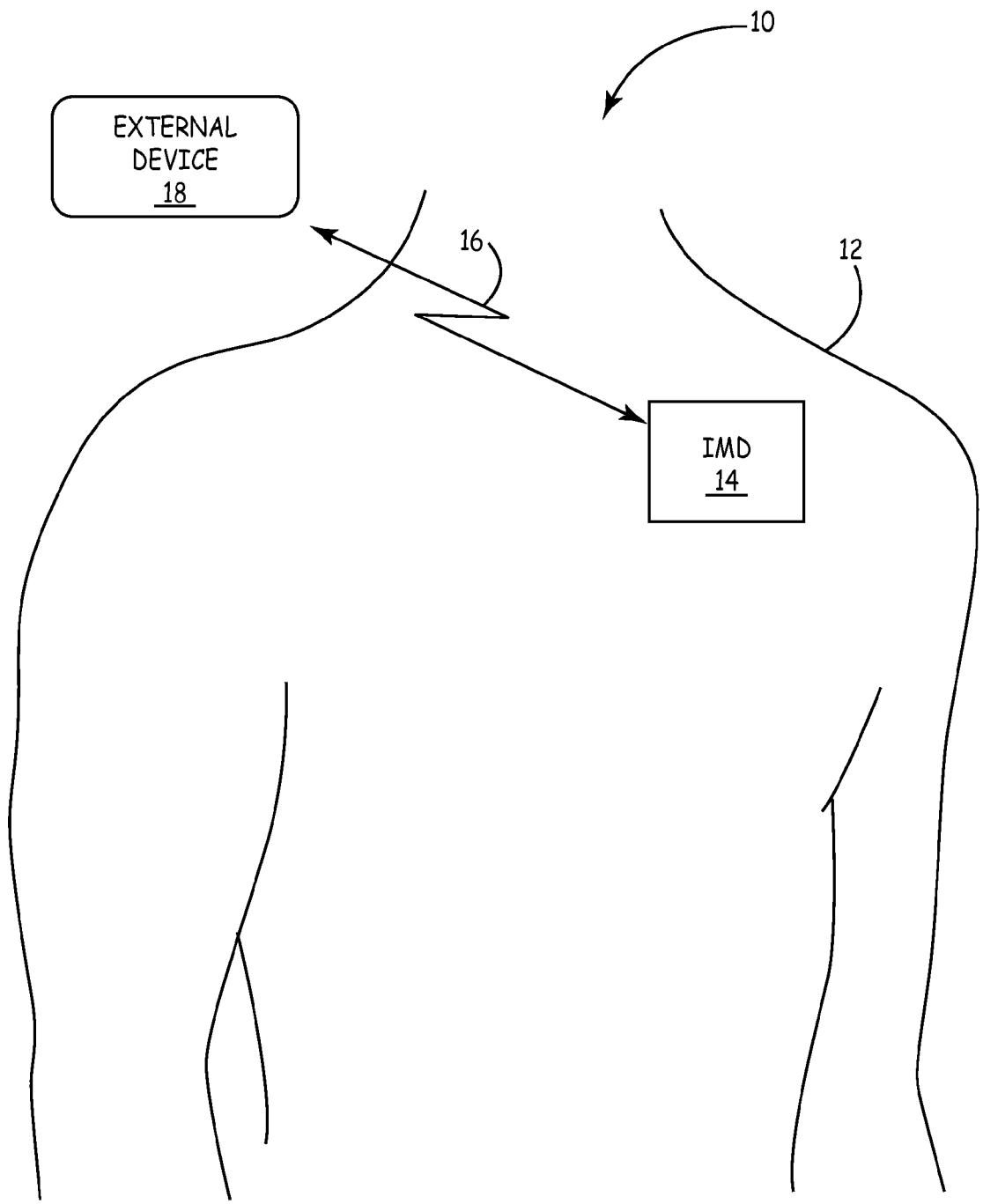
FIG. 1 is a conceptual diagram illustrating an example medical system in which at least one device uses the communication session recovery techniques described in this disclosure.

FIG. 1 is a conceptual diagram illustrating an example medical system 10 in which the wakeup techniques described in this disclosure may be utilized. Medical system 10 includes an implantable medical device (IMD) 14 and an external device 18 that communicate via wireless communication (represented by arrow 16). IMD 14 and external device 18 may communicate with one another by any of a number of wireless communication techniques. Example wireless communication techniques include RF telemetry, but other techniques are also contemplated, including inductive telemetry, magnetic telemetry, acoustic telemetry, or the like.

In one instance, IMD 14 and external device 18 may communicate in accordance with the Medical Implant Communications Service (MICS) band regulation. The MICS band regulation defines communication requirements for the 402-405 MHz frequency band. In accordance with the MICS band regulation, the frequency band is divided into ten channels with each channel corresponding to a 300 kilohertz (kHz) sub-band. Although the techniques of this disclosure are described in the context of the MICS band regulation, IMD 14 and external device 18 may communicate using any frequency band regulation or unregulated frequency band in addition to or instead of the MICS band regulation. As an example, IMD 14 and external device 18 may communicate using the Medical External Data Service (MEDS) frequency band regulation, which defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band.

To establish a communication session, external device 18 typically selects one of the channels of the frequency band to transmit on. To do so, external device 18 may perform a clear-channel assessment (CCA) to select the one of the channels of the frequency band with a lowest ambient power level (e.g., the least-noisy or least-interfered with channel). Performing CCA increases the likelihood that the external device 18 selects an unused channel, thus decreasing the likelihood of interference from multiple communication sessions attempting to use the same channel. In other instances, such as when a different frequency band regulation is used, external device 18 may not perform CCA prior to establishing the communication channel. Instead, the devices may begin to transmit over any channel without regard to noise or use of the channel. Once the external device 18 selects the channel to transmit on (e.g., either by CCA or randomly), external device 18 establishes a communication session with IMD 14 over the selected channel by exchanging one or more packets. As used herein, the establishment of the communication session will generally refer to both channel selection (if performed) and the actual exchange of communications to establish the communication session.

IMD 14 may initiate the establishment of the communication session by sending one or more communications to external device 18. In accordance with techniques of this disclosure, IMD 14 may initiate the establishment of the communication session by sending a wakeup communication to external device 18. In this case, external device 18 may operate in low power state (sometimes referred to as a sleep state or a low current state) in which the external device occasionally powers up a receiver to listen for the wakeup communication from IMD 14. Upon receiving the wakeup communication, external device 18 transitions from the low power state to a high power state to establish the communication session with IMD 14. Operating external device 18 in the low power state when no communication session is established reduces the amount of power consumed by external device 18 when no telemetry is occurring. This may enable external device 18 to be powered by a battery or other limited power supply. A user of external device 18 may also cause external device 18 to transition from the low power state to the high power state to initiate establishment of the communication session with IMD 14, e.g., by interacting with a user interface of external device 18.

Once the communication session is established, external device 18 and IMD 14 transmit communications to or receive communications from one another. External device 18 may, for example, transmit information to IMD 14, such as configuration information that may be used to configure a therapy to be provided to patient 12. IMD 14 may transmit information to the external device 18, including information related to a condition of patient 12, information related to a therapy delivered to patient 12, or information related to a status of one or more components of IMD 14 or components coupled to IMD (e.g., leads). Thus, the communication session may be either uni-directional or bi-directional.

IMD 14 may be any of a variety of medical devices that provide therapy to patient 12, sense physiological or biological conditions of patient 12 or a combination thereof In some instances, IMD 14 may be a device that provides electrical stimulation therapy in the form of cardiac rhythm management therapy to a heart of patient 12. In such a case, IMD 14 may include one or more implantable leads (not shown) with one or more electrodes that extend from IMD 14 for delivering therapy to and/or sensing physiological signals of a heart of patient 12. The leads may be implanted within one or more atria or ventricles of the heart of patient 12 or a combination thereof In other words, IMD 14 may be used for single chamber or multi-chamber cardiac rhythm management therapy. The cardiac rhythm management therapy delivered by IMD 14 may include, for example, pacing, cardioversion, defibrillation and/or cardiac resynchronization therapy (CRT).

In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like to treat various conditions, including movement and affective disorders such as chronic pain, Parkinson's disease, tremor and dystonia, urinary storage and voiding dysfunction, digestion dysfunction, sexual dysfunction or the like.

In further instances, IMD 14 may be a device that delivers a drug or therapeutic agent to patient 12 via an implantable catheter (not shown). IMD 14 may, for example, be implanted within a subcutaneous pocket in an abdomen of patient 12 and the catheter may extend from IMD 14 into the stomach, pelvic floor, brain, intrathecal space of the spine of patient 12 or other location depending on the application. IMD 14 may deliver the drug or therapeutic agent via the catheter to reduce or eliminate the condition of the patient and/or one or more symptoms of the condition of the patient. For example, IMD 14 may deliver morphine or ziconotide to reduce or eliminate pain, baclofen to reduce or eliminate spasticity, chemotherapy to treat cancer, or any other drug or therapeutic agent to treat any other condition and/or symptom of a condition.

As one example, IMD 14 may be a wireless sensor implanted within patient 12 to sense one or more physiological signals of patient 12. IMD 14 may be implanted at targeted monitoring sites and transmit the sensed signals, thus avoiding limitations associated with lead-based sensors. In some instances, IMD 14 uses the sensed physiological signals to monitor a condition of patient 12 or provide therapy to patient 12 as a function of the sensed physiological signals. Alternatively, or additionally, IMD 14 transmits the sensed physiological signals to another device, such as another implanted device or external device 18, which may in turn monitor the condition of patient 12 or provide therapy to patient 12 as a function of the sensed physiological signals. IMD 14 may sense, sample, and process one or more physiological signals such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter.

External device 18 may be a programming device or monitoring device that allows a user, e.g., physician, clinician, technician or patient, to configure a therapy delivered by IMD 14 or to retrieve data sensed by IMD 14. External device 18 may include a user interface that receives input from the user and/or displays data to the user, thus allowing the user to view data retrieved from IMD 14 or program the sensing or therapy parameters of IMD 14.

External device 18 may be a dedicated hardware device with dedicated software for programming or otherwise communicating with IMD 14. Alternatively, external device 18 may be an off-the-shelf computing device running an application that enables external device 18 to program or otherwise communicate with IMD 14. In one example, external device may be a physician programmer located within a clinic or other medical setting. In another example, external device 18 may be a handheld computing device that may be attached to or otherwise carried by patient 12, such as a pager, watch, patch, band, finger clip or the like. Alternatively, external device 18 may be a computer workstation, such as a CareLink® monitor, available from Medtronic, Inc. of Minneapolis, Minn.

Figure 2:
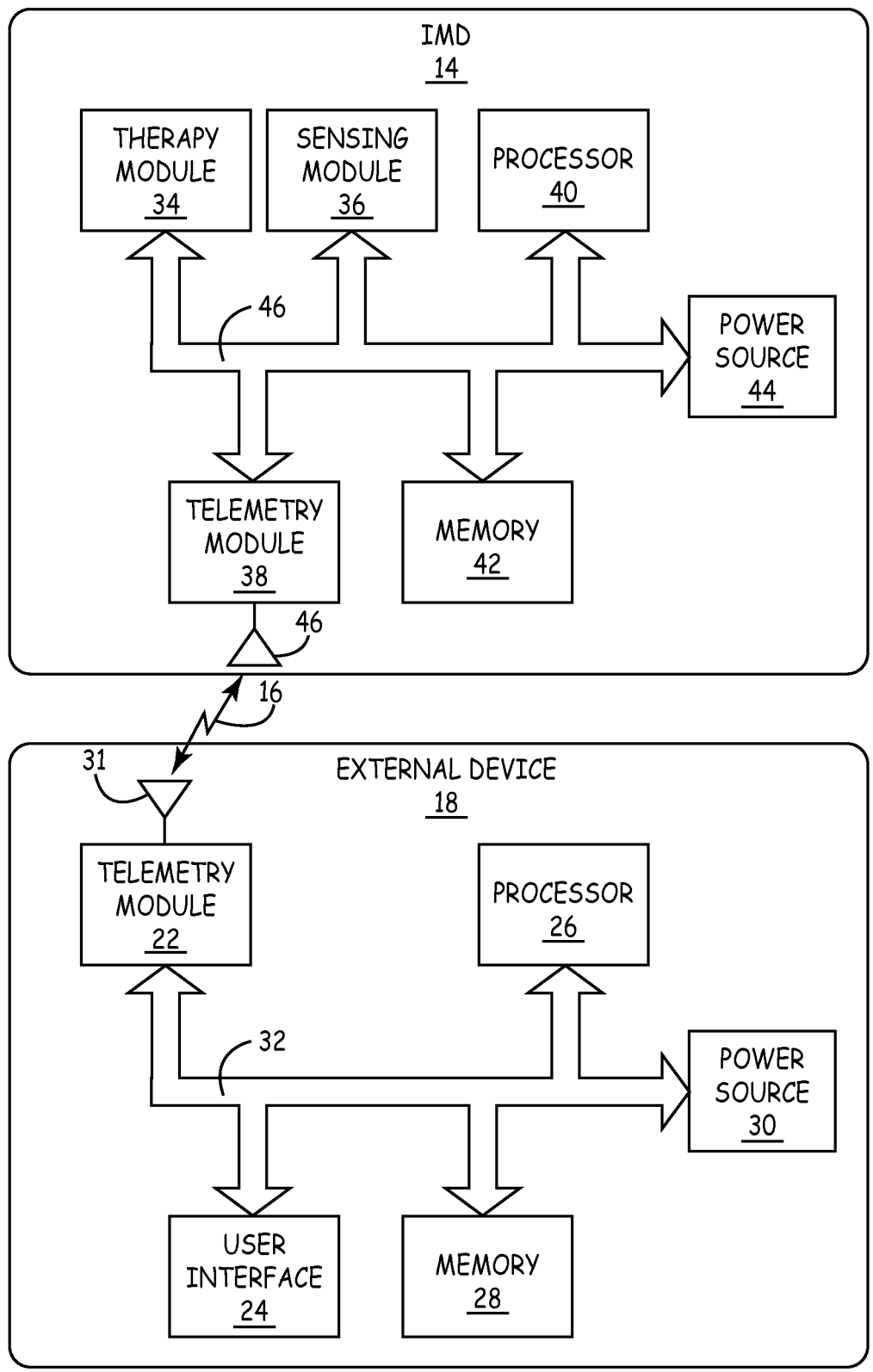
FIG. 2 is a block diagram illustrating an example IMD and external device in further detail.

FIG. 2 is a block diagram illustrating IMD 14 and external device 18 in further detail. As illustrated in the example of FIG. 2, IMD 14 includes a therapy module 34, sensing module 36, telemetry module 38, processor 40, memory 42 and power source 44. External device 18 includes a telemetry module 22, user interface 24, processor 26, memory 28 and power source 30. The components of IMD 14 and external device 18 may be interconnected by data buses 46 and 32, respectively, or by one or more direct electrical connections.

Power source 30 of external device 18 may hold a limited amount of power. Power source 30 may, for example, be a rechargeable or non-rechargeable battery. In either case, the amount of power of the battery is limited before the battery needs to be recharged or replaced. As such, it may be desirable to reduce power consumption by the components of external device 18.

Conventional IMD programming devices include a power cord or cable that plugs into an alternating current (AC) source (e.g., a wall outlet). Because the AC source is capable of providing unlimited power, conventional programming devices do not typically have to be designed for low power consumption. For example, a receiver of a conventional programming device may continuously listen for communications from IMD 14. In other words, the receiver continuously consumes power to listen for the communications from IMD 14. In the case of external device 18, which has a limited power supply, low power consumption is desired to extend a service life of power source 30, i.e., extend the operating time between charging or replacement of power source 30.

The techniques of this disclosure reduce the amount of power consumed by telemetry module 22 of external device 18, thus increasing the amount of time between charging or replacement of power source 30. In accordance with the techniques of this disclosure, telemetry module 22 of external device 18 operates in a low power state (e.g., sleep state or low current state). In the low power state, telemetry module 22 interleaves intervals during which telemetry module 22 is powered down with intervals during which telemetry module 22 is powered up to listen for a wakeup communication from IMD 14. Telemetry module 38 of IMD 14 transmits a wakeup communication to telemetry module 22 of external device 18. In one example, telemetry module 38 transmits the wakeup communication in response to detecting a medical event. In response to receiving the wakeup communication from IMD 14, telemetry module 22 begins to operate in a high power state that consumes more power than the low power state. In the high power state, telemetry module 22 of external device 18 exchanges communications with IMD 14 to establish a communication session. During the high power state, telemetry modules 22 and 38 exchange at least some communications using a native communication mode. Telemetry modules 22 and 38 consume more power while operating in the native communication mode than when operating in a wakeup communication mode used to transmit and receive the wakeup communications.

Telemetry module 22 of external device 18 communicates wirelessly with telemetry module 38 of IMD 14 by any of a number of wireless communication techniques. Example wireless communication techniques include RF telemetry, but other techniques are also contemplated, including inductive telemetry, magnetic telemetry, acoustic telemetry, or the like. To this end, telemetry module 22 and telemetry module 38 may include any suitable hardware, firmware, software or any combination thereof for wireless communication. For example, telemetry module 22 and telemetry module 38 may include appropriate modulation, demodulation, frequency conversion, filtering, and amplifier components for transmission and reception of data, including radio frequency (RF) components and antennas 31 and 46, as applicable.

External device 18 of FIG. 2 also includes a user interface 24 via which a user may interact with external device 18. The user may, for example, interact with user interface 24 to cause external device 18 to transition from the low power state to the high power state, e.g., to establish a communication session with IMD 14. In this case, the communication session may be initiated by the user instead of via a wakeup communication sent from IMD 14. User interface 24 may include an input mechanism, such as a keypad, a peripheral pointing device, a touch screen, microphone or the like, and an output mechanism, such as a display (e.g., a cathode ray tube (CRT) display, a liquid crystal display (LCD) or light emitting diode (LED) display), speaker or the like.

External device 18 also includes a processor 26 that controls operation of the components of external device 18. External device 18 further includes a memory 28. Memory 28 may include computer-readable instructions that, when executed by processor 26, cause external device 18 to perform various functions attributed to external device 18 herein. Memory 28 may also store data input by the user via user interface 24 (e.g., therapy parameters or the like) as well as data retrieved from IMD 14 via telemetry communication (e.g., sensed data, device data or the like).

IMD 14 of FIG. 2 includes a sensing module 36 and a therapy module 34. As such, IMD 14 illustrated in FIG. 2 may provide both sensing and therapy functionality. Although FIG. 2 includes both sensing module 36 and therapy module 34, IMD 14 may only provide sensing functionality and no therapy as in the case of an implantable loop recorder. In such cases, IMD 14 may not include therapy module 34. Alternatively, IMD 14 may provide therapy with no sensing. In such cases, IMD 14 may not include sensing module 36.

Sensing module 36 is configured to monitor one or more physiological signals using one or more sensors connected to sensing module 36. In one example, sensing module 36 is configured to monitor signals sensed by one or more of electrodes on leads extending from IMD 14. In another example, sensing module 36 may be configured to monitor signals sensed by a sensor within or on IMD 14. In a further example, sensing module 36 may be configured to receive signals sensed by one or more wireless or lead-less sensors and transmitted wirelessly to IMD 14. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter.

Sensing module 36 may store the sensed signals in memory 42. In some instances, sensing module 36 may store the sensed signals in raw form. In other instances, sensing module 36 may process the sensed signals and store the processed signals in memory 42. For example, sensing module 36 may amplify and filter the sensed signal and store the filtered signal in memory 42. The signals stored by sensing module 36 may, in some cases, be retrieved and further processed by processor 40.

IMD 14 may also provide therapy, such as electrical stimulation therapy or drug delivery therapy, to patient 12 in accordance with parameters of one or more selected therapy programs. In particular, processor 36 controls therapy module 34 to deliver therapy to patient 12 according to one or more therapy programs, which may be received from external device 18 and stored in memory 42. In the case of electrical stimulation therapy, therapy module 34 may include a stimulation generator that generates and delivers electrical stimulation therapy, e.g., in the form of pulses or shocks. Processor 40 may control the stimulation generator to deliver electrical stimulation pulses with amplitudes, pulse widths, frequency, and/or electrode polarities specified by the one or more therapy programs. In the case of drug delivery therapy, therapy module 34 may include a pump that delivers a drug or therapeutic agent to patient 12. Processor 40 may control the pump to deliver the drug or therapeutic agent with the dosage and frequency (or rate) specified by the one or more therapy programs.

Power source 44 of IMD 14 delivers operating power to the components of external device 18. Power source 44 may include a rechargeable or non-rechargeable battery. A non-rechargeable battery may be selected to last for several years, while a rechargeable battery may be charged from an external charging device on a daily or weekly basis. In either case, especially in the case of the non-rechargeable battery, the amount of power of the battery is limited before requiring recharging or replacement.

Processor 40 may control operation of IMD 14, e.g., by controlling operation of the various components of IMD 14. Memory 42 may include computer-readable instructions that, when executed by processor 40, cause IMD 14 to perform various functions attributed to the components of external device 18 herein. Memory 28 may also store sensed data and operating parameters received via telemetry from external device 18.

Processors 26 and 40 may include one or more of a microprocessor, a controller, a DSP, an ASIC, an FPGA, or equivalent discrete or integrated logic circuitry. In some examples, processors 26 and 40 may include multiple components, such as any combination of one or more microprocessors, one or more controllers, one or more DSPs, one or more ASICs, or one or more FPGAs, as well as other discrete or integrated logic circuitry. The functions attributed to processor 26 and 40 herein may be embodied as software, firmware, hardware or any combination thereof. Memory 28 and 42 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media or a combination thereof.

IMD 14 and external device 18 are illustrated for exemplary purposes. IMD 14 and external device 18 may include more or fewer components than shown in FIG. 2 depending on the application of the devices. As such, the techniques described in this disclosure should not be limited by the example devices illustrated in FIG. 2.

Figure 3:
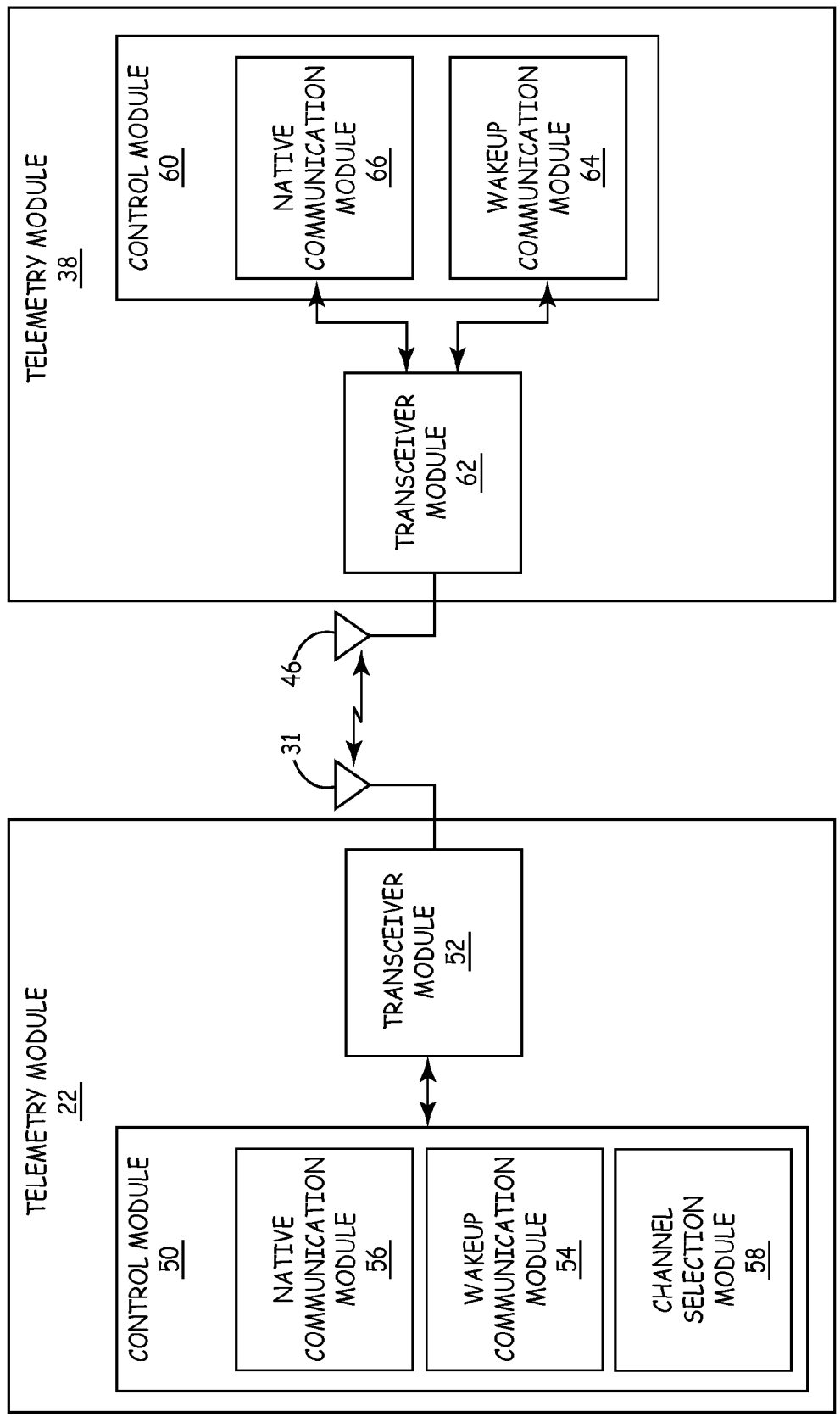
FIG. 3 is a block diagram illustrating telemetry modules of the IMD and external device of FIG. 2 in further detail.

FIG. 3 is a block diagram illustrating telemetry modules 22 and 38 in further detail. Telemetry module 22 of external device 18 includes a control module 50 and a transceiver module 52. In the example of FIG. 3, control module 50 includes a wakeup communication module 54 and a native communication module 56, which transmit or receive communications in a wakeup communication mode and native communication mode respectively. Control module 50 also includes a channel selection module 58 that selects a channel over which to transmit and receive communications. In some instances, channel selection module 58 may be integrated within native communication module 56. Transceiver module 52 is coupled to antenna 31.

Telemetry module 38 of IMD 14 includes a control module 60 and a transceiver module 62. Control module 60 further includes a wakeup communication module 64 and a native communication module 66, which transmit or receive communications in a wakeup communication mode and native communication mode respectively. Transceiver module 62 is coupled to antenna 46.

Telemetry module 38 of IMD 14 may transmit a wakeup communication to initiate the establishment of a communication session with external device 18. The wakeup communication may include one or more wakeup packets that indicate to telemetry module 22 of external device 18 that it should transition from the low power state to the high power state and establish a communication session with IMD 14. Telemetry module 38 of IMD 14 may transmit the wakeup packets for a duration of time that is at least slightly longer than the sniff interval of telemetry module 22 of external device 18. The wakeup packets are communicated in a wakeup communication mode that corresponds with an encoding scheme, transmission or data rate, packet size and/or packet structure, frequency, or the like.

In some instances, telemetry module 38 of IMD 14 may generate and transmit the wakeup packets in response to IMD 14 detecting a medical event. In cases in which IMD 14 and external device 18 communicate in accordance with the MICS band regulation, the initiating device may be required to perform CCA before initiating communication to avoid interference with other MICS transmissions. However, the MICS band regulation includes an exception when a medical event occurs. In this case, no CCA is required before initiating communication. The detected medical event may be an occurrence or the lack of an occurrence recognized by IMD 14 as requiring the transmission of data from IMD 14 to external device 18 to protect the safety or well being of patient 12 in whom IMD 14 is implanted. As such, wakeup communication module 64 may generate one or more wakeup packets in response to detecting the medical event and transmit the one or more wakeup packets via transceiver module 62 and antenna 46. Other frequency band regulations or non-regulated frequency bands may not require CCA before initiating communication, in which case wakeup communication module 64 of IMD 14 may transmit the one or more wakeup communications any time it desires to initiate communication, e.g., periodically once a day or the like.

Telemetry module 22 of external device 18 may operate in a low power state. While operating in the low power state, telemetry module 22 of external device 18 interleaves intervals during which one or more components of telemetry module 22 are powered down with intervals during which the one or more components are powered up. During the intervals in which the components of telemetry module 22 are powered up, wakeup communication module 54 monitors signals received by transceiver module 52 for a wakeup communication (or wakeup packet), a process sometimes referred to as "sniffing." The components of telemetry module 22 may power up at periodic intervals to monitor for the wakeup packet. In one example, the components of telemetry module 22 may power up every two seconds to monitor the one or more channels for a wakeup packet. The sniff interval, i.e., the interval between power ups, may be set to be a longer or shorter period of time than two seconds and may be on the order of milliseconds, minutes, hours or the like. Alternatively, the components of telemetry module 22 may be powered up at non-periodic intervals. Operating telemetry module 22 in the low power state reduces the amount of power consumed by telemetry module 22 when no communication session is active, thus increasing the amount of time between charging or replacement of power source 30.

In some aspects, wakeup communication module 54 may analyze the signal received by transceiver module 52 in a plurality of phases or stages to monitor for a wakeup signal. Each of the phases or stages may consume additional power. In some instances, each of the previous stages may be required to be satisfied before the subsequent stage is invoked. If each of the phases or stages are met (i.e., the signal received by transceiver module 52 satisfies particular criteria of the stage), a valid wakeup signal is detected. If any of the stages is not met, any remaining stages are aborted, in which case the components of telemetry module 22 are powered down again.

In one example, a first detection phase may be a power level comparator. The first detection phase will abort when the received signal strength indication (RSSI) average for a given signal, or other power level indicator of the signal, is not above a threshold level. This technique may block most ambient channel noise from passing through the first detection phase. On passing the first detection phase, the received signal will be subjected to a second detection phase that may monitor an Integrated Frequency Deviation. The second detection phase may, for example, estimate the frequency deviation of the incoming signal and compare this with both high and low thresholds. Continuous Wave (CW) signals will "abort low" based on near-zero frequency deviation. Ambient noise signals which passed through the first detection phase, as well as other high bandwidth signals, will abort high. On passing through the second detection phase, the received signal will be subjected to a third detection phase. The third detection phase demodulates the signal and counts the number of Manchester-encoding errors. The third detection phase will abort when the number of Manchester errors exceeds a threshold. When the number of errors does not exceed the threshold, a valid wakeup signal is detected.

Other multi-phased or multi-staged wakeup detection techniques may be used, however. For example, each of the phases may be initiated concurrently and may all be aborted in response to the received signal not meeting the requirements of any one of the phases. Other example phased wakeup detection techniques are described in copending U.S. patent application Ser. No. 12/242,789 to LeReverend et al. and copending U.S. patent application Ser. No. 12/242,782 to LeReverend et al., both of which are incorporated herein in their entirety. In any case, performing the monitoring operations in a plurality of stages or phases to monitor for the wakeup signal enables quick abortion of the monitoring on a channel when early stage requirements are not met, thus further reducing power consumption during the wakeup process.

Telemetry module 22 of external device 18 transitions from the low power state to a high power state in response to receiving a wakeup packet from IMD 14. In the high power state, power consumption by the components of external device 18 is greater than in the low power state. For example, the components of external device 18 may be continuously powered up during the high power state. As another example, the components of external device 18 may be powered up with a different duty cycle in which the components are powered more often than in the low power state.

Upon transitioning to the high power state, telemetry module 22 of external device 18 establishes a communication session with telemetry module 38 of IMD 14. Telemetry modules 22 and 38 may establish the communication session in accordance with the requirements of the frequency band regulation via which the devices are communicating and/or in accordance with one or more wireless communication protocols via which the devices are communicating.

In one example, telemetry module 22 selects one of the channels of the frequency band to transmit on, e.g., via a CCA as required in the MICS band regulation. Although described below as performing CCA to select a channel, telemetry module 22 may, in some instances, begin transmitting data over a channel without performing CCA. However, performing CCA increases the likelihood that the external device 18 selects an unused channel, thus reducing the likelihood of interference from multiple communication sessions attempting to use the same channel. Such schemes may be particularly useful in an environment in which a number of medical devices are communicating using a limited number of channels, e.g., in a hospital, nursing home, doctor's office, or the like.

During CCA, channel selection module 58 may monitor at least a portion of the channels of the frequency band(s) and select one of the channels that meet a particular condition. In one example, channel selection module 58 monitors all of the channels and selects the channel with the lowest ambient power level (the least-noisy or least-interfered with channel)

as the channel to transmit on. In another example, channel selection module 58 assesses at least a portion of the channels of the frequency band, and in some instances all of the channels of the frequency band, as a function of the ambient power on the respective channels and the ambient power on at least one other channel, e.g., the two immediately adjacent channels. Such a technique is described in copending U.S. patent application Ser. No. 12/414,946 to Corndorf, which is incorporated herein by reference in its entirety. In another example, channel selection module 58 may monitor the channels of the frequency band and select a first channel having an ambient power level below a minimum power level threshold.

Telemetry module 22 of external device 18 establishes the communication session with IMD 14 over the selected channel. Native communication module 56 may, for example, generate one or more open request packets (or other native mode packets) and provide the open request packets to transceiver module 52 for transmission on the selected channel. The one or more packets are transmitted in a native communication mode that corresponds with an encoding scheme, a transmission or data rate, a packet size and/or structure, frequency or the like. As will be described in more detail, the native communication mode may have a more complex encoding scheme, faster transmission or data rate, larger packet sizes, and/or more complex packet structures than the wakeup communication mode. The packets sent from external device 18 indicating the desire to establish a communication session will be referred to in this disclosure as "open request packets."

In this case, IMD 14 may monitor the plurality of channels in the native communication mode. Telemetry module 38 of IMD 14 may, for example, interleave periods in which telemetry module 38 monitors for native mode communications with the periods in which telemetry module 38 sends the wakeup communications to external device 18. If IMD 14 was operating in a low power state (similar to that described above for external device 18), IMD 14 may transition from the low power state to a high power state upon detecting the medical event that triggered transmission of the wakeup communication to transmit the wakeup communications to and monitor for native mode communications from external device 18.

In other instances, telemetry module 38 of IMD 14 may not monitor the channels in the native communication mode. Instead, telemetry module 38 may monitor for a wakeup packet. In one example, telemetry module 38 of IMD 14 may interleave periods in which telemetry module 38 monitors for the wakeup communications from external device 18 with the periods in which telemetry module 38 transmits wakeup communications to external device 18. In another example, telemetry module 38 may transition back to the low power state after transmitting the wakeup communications to external device 18 and begin monitoring for wakeup communications in the low power state. Telemetry module 38 of IMD 14 may, in some instances, monitor for the wakeup packet using the multi-stage or multi-phase wakeup process.

Telemetry module 22 of external device 18 may transmit a wakeup communication, e.g., one or more wakeup packets, to IMD 14 before sending the one or more open request packets. In other words, telemetry module 22 of external device 18 may transmit one or more wakeup packets in response to receiving the wakeup packet from IMD 14. Wakeup communication module 54 may generate the one or more wakeup packets and provide the packets to transceiver module 52 for transmission via antenna 31. Telemetry module 22 of external device 18 may transmit wakeup packets for a duration of time that is at least slightly longer than the sniff interval of telemetry module 38 of IMD 14. The wakeup packets may be generated and transmitted in the wakeup communication mode.

In response to receiving a wakeup packet, telemetry module 38 may again transition from the low power state to a high power state and begin to monitor for an open request packet or other native mode packet. For example, the one or more components that were powered down or in a low current state are powered up for operation. One such component may be native communication module 66. Native communication module 66 begins to monitor for the open request packet on the channel on which the wakeup packet was received or on a channel specified within the wakeup packet.

In response to receiving one of the open request packets, IMD 14 may transmit one or more packets confirming its receipt of the open request packet and confirming its desire to establish the communication session with external device 18. The packets sent from IMD 14 in response to the open request packets are also sent in the native communication mode and are referred to herein as "open response packets." The open response packets may be generated by native communication module 66 and provided to transceiver module 62 for transmission to external device 18 on the channel identified in the open response packet or on the channel on which the open response packet was received.

Native communication module 56 monitors for an open response packet from IMD 14. If no open response packet is received from IMD 14, telemetry module 22 may reattempt to establish the communication session by either sending additional open response packets and/or additional wakeup packets or determine that no communication session can be established at this time. If an open response packet is received from IMD 14, the communication session is established on the selected channel.

Once the communication session is established, telemetry module 22 of external device 18 and telemetry module 38 of IMD 14 may exchange data with one another. As described above, external device 18 may transmit configuration information to IMD 14 that may be used to configure a therapy to be provided to patient 12, e.g., parameters of one or more selected therapy programs. IMD 14 may transmit sensed physiological parameters, diagnosis generated based on the sensed physiological parameters, a log of delivered therapies, information regarding the amount of remaining battery power or other status indicator, or other data to external device 18. The exchange of data between telemetry module 22 and 38 is done in the native communication mode.

As described above, the transmission and reception of different types of packets (e.g., wakeup packets vs. data packets) may performed using the different communication modes, which may include different encoding schemes, different transmission or data rates, different packet sizes, different packet structures, frequency, or the like. In one example, the wakeup communication mode uses Manchester encoding, a data rate of 6.4 Kbps, and a packet size of 25 bytes and a less complicated packet structure while the native communication mode uses DQPSK or DBPSK encoding, a data rate of greater than 48 Kbps, a packet size of greater than 47 bytes and a more complicated packet structure. As such, a less complicated communication mode (i.e., the wakeup communication mode) is used to transition external device 18 or IMD 14 from a low power state to a high power state and the more complex communication mode (i.e., the native communication mode) is used to establish the communication session as well as exchange data over the established communication session. In other instances, external device 18 may be manually transitioned from the low power state to the high power state to establish a communication session with IMD 14, e.g., in response to an input from a user of external device 18.

Transceiver modules 52 and 62 transmit and receive signals, e.g., via radio frequency (RF) communication, via antennas 31 and 46, respectively. Transceiver modules 52 and 62 may include a receiver, a transmitter or both a receiver and transmitter. Transceiver module 52 may include any suitable hardware, firmware, software or any combination thereof for transmitting signals, including appropriate modulation, demodulation, frequency conversion, filtering, and amplifier components for transmission and reception of data.

Figure 4:
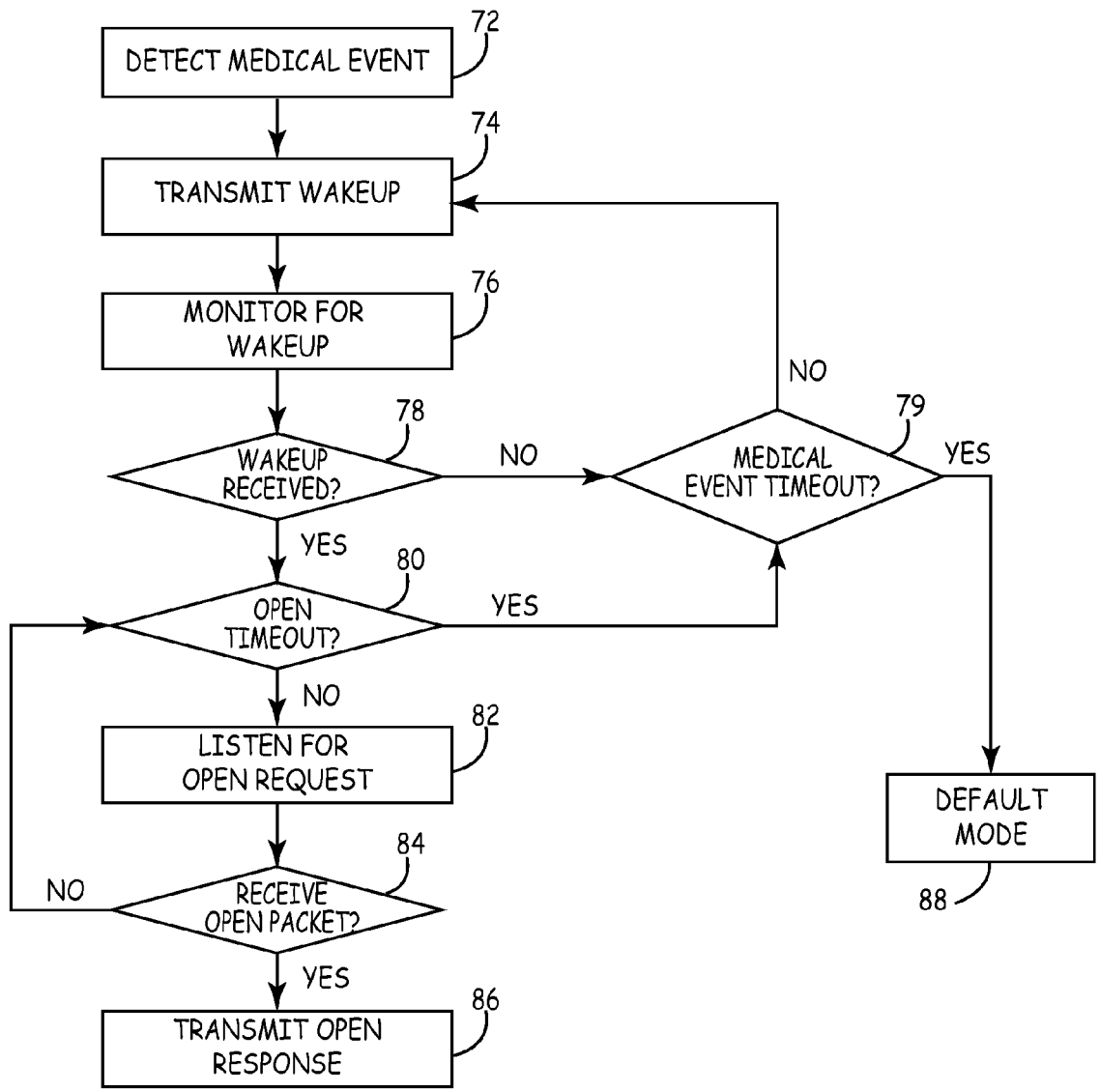
FIG. 4 is a flow diagram illustrating example operation of a telemetry module of an IMD initiating establishment of a communication session in accordance with one embodiment of this disclosure.

FIG. 4 is a flow diagram illustrating example operation of telemetry module 38 of IMD 14 in accordance with one embodiment of this disclosure. IMD 14 detects a medical event (72). The detected medical event may be an occurrence or lack of an occurrence recognized by IMD 14 as requiring the transmission of data from IMD 14 to external device 18 to protect the safety or well being of patient 12 in whom IMD 14 is implanted. For example, IMD 14 may detect that a lead impedance is outside of an acceptable range, that a therapy regimen has been exhausted without termination of an arrhythmia, an AF burden above a programmed threshold, or any of a variety of events that are classified as medical events. In other instances, e.g., in instances in which the band regulation does not require CCA, IMD 14 may detect a desire to communicate with external device.

In response to detecting the medical event or other desire to communicate, telemetry module 38 of IMD 14 generates and transmits one or more wakeup packets (74). For example, telemetry module 38 may generate and send the wakeup packets over a plurality of different channels (e.g., the ten channels of the MICS band). Telemetry module 38 of IMD 14 may transmit the wakeup packets for a duration of time that is at least slightly longer than the sniff interval of telemetry module 22 of external device 18. The wakeup packets are communicated in a wakeup communication mode that is different, than the native communication mode utilized by the telemetry modules. The wakeup communication mode may, for example, have a less complicated encoding scheme, slower transmission or data rate, smaller packet sizes, and/or simpler packet structures than the native communication mode.

Telemetry module 38 of IMD 14 may also interleave periods during which a receiver of telemetry module 38 monitors for wakeup communications with the periods during which a transmitter sends the wakeup communications (76). In the case in which telemetry module 38 transmits wakeup packets over a plurality of channels, telemetry module 38 may interleave periods during which the receiver of telemetry module 38 monitors for the wakeup communications on one or more of the channels. For example, during telemetry module 38 may transmit one or more wakeup packets on channel 1 of the MICS band, monitor for a wakeup packet on all of the channels (or a subset of channels), transmit one or more wakeup packets on channel 2 of the MICS band, monitor for a wakeup packet on all of the channels (or a subset of channels), transmit one or more wakeup packets on channel 3 of the MICS band, monitor for a wakeup packet on all of the channels (or a subset of channels), and so on. As such, telemetry module 38 of IMD 14 transitions from a low power state to a high power state to transmit and/or listen for wakeup communications in response to the detected medical event.

When telemetry module 38 does not receive a wakeup packet during the period in which the receiver listens for a communication ("NO" branch of block 78), telemetry module 38 determines whether a medical event timeout is detected (79). To this end, telemetry module 38 may initialize a medical event timer upon detecting the medical event. The medical event timeout is detected upon either the medical event timer reaching zero (in the case of a count down timer) or the medical event timer reaching a threshold value (in the case of a count up timer). The medical event timer may be initialized such that telemetry module 38 at least has enough time to transmit wakeup packets on each of the plurality of channels before the medical event timeout occurs.

When the medical event timeout is not detected ("NO" branch of block 79), telemetry module 38 continues to transmit and/or monitor for wakeup communications as described above with respect to blocks 74 and 76, respectively. When the medical event timeout is detected ("YES" branch of block 79), telemetry module 38 enters a default communication mode (88). Telemetry module 38 may, for example, transition back to the low power state and begin to monitor for wakeup communications in the low power state.

When telemetry module 38 receives a wakeup packet ("YES" branch of block 78), telemetry module 38 determines whether a open (or native mode) timeout has been detected (80). To this end, telemetry module 38 may initialize an open timer to track the amount of time since receiving the wakeup packet from external device 18. In the case of a count down timer, the timeout is detected upon the open timer reaching zero. In the case of a count up timer, the timeout is detected upon the open timer reaching a threshold value. The open timeout prevents telemetry module 38 of IMD 14 from operating in a high power telemetry state for an extended period of time.

When no open timeout is detected ("NO" branch of block 80), telemetry module 38 begins to monitor for a native mode packet, such as an open request packet (82). Telemetry module 38 may begin to listen for native mode packets on the channel on which the wakeup packet was received or on a channel specified within the wakeup packet. The native mode packets may have a more complex encoding scheme, faster transmission or data rate, larger packet sizes, and/or more complex packet structures than the wakeup communication mode. When telemetry module 38 does not receive an open request packet during the listen period ("NO" branch of block 84), telemetry module 38 again determines whether the open timeout is detected. When the open time out is detected ("YES" branch of block 80), telemetry module 38 determines whether the medical event timeout is detected as described above with respect to block 79.

When telemetry module 38 does receive the open request packet ("YES" branch of block 84), transmits one or more open response packets (86). Like the open request packets, the open response packets are native mode packets. Once at least one of the open response packets are received by external device 18, the communication session is established and data may be exchanged between IMD 14 and external device 18.

Figure 5:
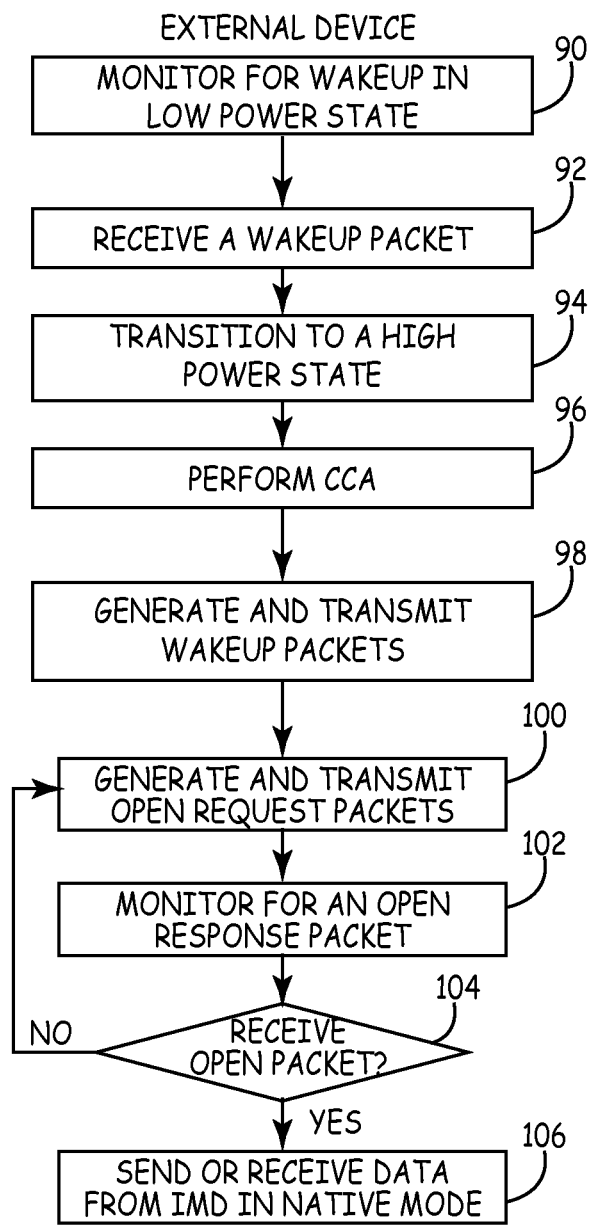
FIG. 5 is a flow diagram illustrating example operation of a telemetry module of an external device establishing a communication session in accordance with one embodiment of this disclosure.

FIG. 5 is a flow diagram illustrating example operation of telemetry module 22 of external device 18 in accordance with one embodiment of this disclosure to establish a communication session with IMD 14. Telemetry module 22 may, for example, operate in accordance with the flow diagram of FIG. 5 to establish a communication session with an IMD 14 that is operating in accordance with the flow diagram of FIG. 4. Telemetry module 22 initially monitors for a wakeup communication in a low power state (90). While operating in the low power state, telemetry module 22 of external device 18 interleaves intervals during which one or more components of telemetry module 22 are powered down with intervals during which the one or more components are powered up. When powered up, wakeup communication module 54 monitors signals received by transceiver module 52 for a wakeup packet.

Telemetry module 22 receives at least one wakeup packet transmitted from IMD 14 (92). In response to receiving the at least one wakeup packet, telemetry module 22 transitions from the low power state to a high power state (94). Telemetry module 22 performs a CCA to select one of the channels of the frequency band to transmit on (96).

As described in detail in FIG. 3, the CCA monitors at least a portion of the channels of the frequency band and select one of the channels that meet a particular condition, thus reducing the likelihood of interference with communications between other devices. Although in the example illustrated in FIG. 5 external device 18 performs CCA to select a channel, telemetry module 22 may begin transmitting data over a channel without performing CCA if permitted by the frequency band regulations.

Telemetry module 22 of external device 18 transmits one or more wakeup packets to IMD 14 (98). Telemetry module 22 of external device 18 may transmit the wakeup packets on the channel selected during the CCA or on a different channel. If telemetry module 22 transmits the wakeup packets on a channel other than the selected channel, the wakeup packet may specify the channel selected during the CCA. Telemetry module 22 of external device 18 may transmit wakeup packets for a duration of time that is at least slightly longer than a sniff interval of telemetry module 38 of IMD 14.

Telemetry module 22 transmits one or more open request packets on the selected channel after transmitting the one or more wakeup packets (100). The one or more open request packets are transmitted in the native communication mode, which may have a more complex encoding scheme, faster transmission or data rate, larger packet sizes, and/or more complex packet structures than the wakeup communication mode.

Telemetry module 22 monitors for an open response packet (102). Telemetry module 22 may interleave periods during which it transmits the open request packets with periods in which it monitors for open response packets. When no open response packet is received ("NO" branch of block 104), continues to transmit one or more open request packets and monitors for open response packets as described in blocks 100 and 102, respectively. When external device 18 receives an open response packet from IMD 14 ("YES" branch of block 104), the communication session is established on the selected channel and telemetry module 22 of external device 18 and telemetry module 38 of IMD 14 may exchange data with one another via the established communication session (106). The exchange of data between telemetry modules 22 and 38 may be done in the native communication mode.

Figure 6:
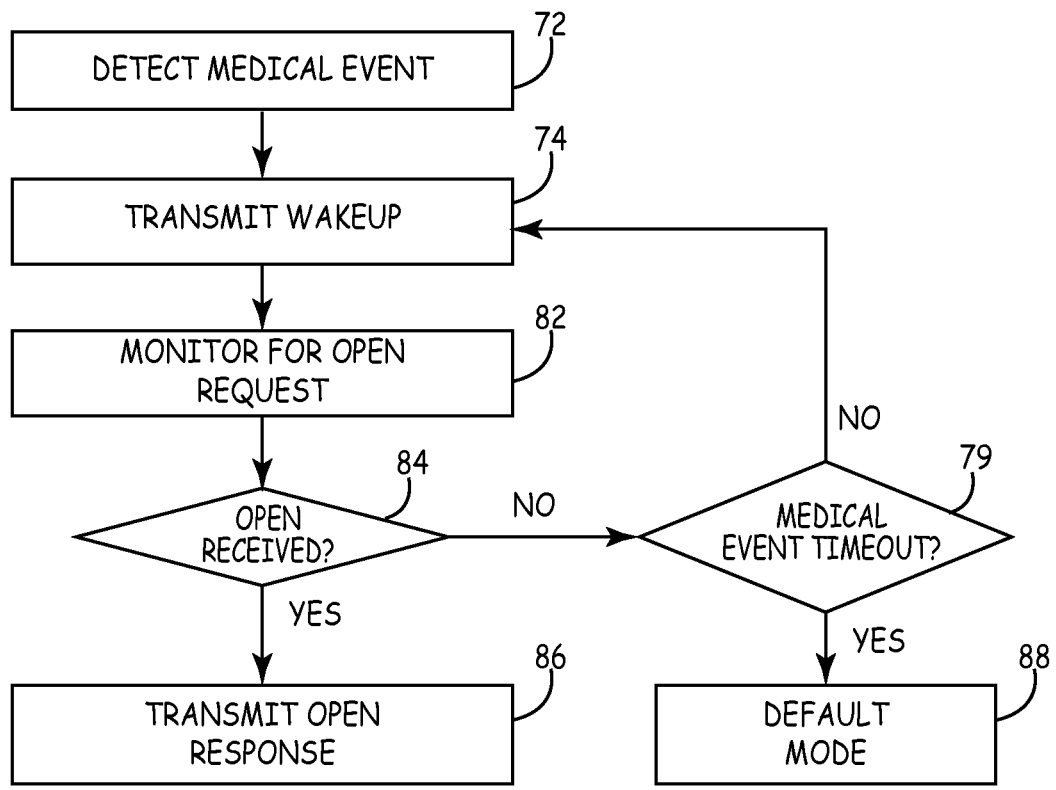
FIG. 6 is a flow diagram illustrating example operation of a telemetry module of an IMD initiating establishment of a communication session in accordance with another embodiment of this disclosure.

FIG. 6 is a flow diagram illustrating example operation of telemetry module 38 of IMD 14 in accordance with another embodiment of this disclosure. Blocks with similar numbers to those of FIG. 4 perform similar functions. Initially, IMD 14 detects a medical event (72). In response to detecting the medical event or other desire to communicate, telemetry module 38 of IMD 14 transmits one or more wakeup packets (74). Telemetry module 38 of IMD 14 may also interleave periods during which a receiver of telemetry module 38 monitors for native mode communications (e.g., open request packets) with the periods during which a transmitter sends the wakeup communications (82).

When telemetry module 38 does not receive an open request packet during the period in which the receiver listens for a communication ("NO" branch of block 84), telemetry module 38 determines whether a medical event timeout is detected (79). When the medical event timeout is not detected ("NO" branch of block 79), telemetry module 38 continues to transmit wakeup communications and/or monitor for open request communications as described above with respect to blocks 74 and 82, respectively. When the medical event timeout is detected ("YES" branch of block 79), telemetry module 38 enters a default communication mode, one of which is described above (88).

When telemetry module 38 does receive the open request packet ("YES" branch of block 84), transmits one or more open response packets (86). Once at least one of the open response packets are received by external device 18, the communication session is established and data may be exchanged between IMD 14 and external device 18.

Figure 7:
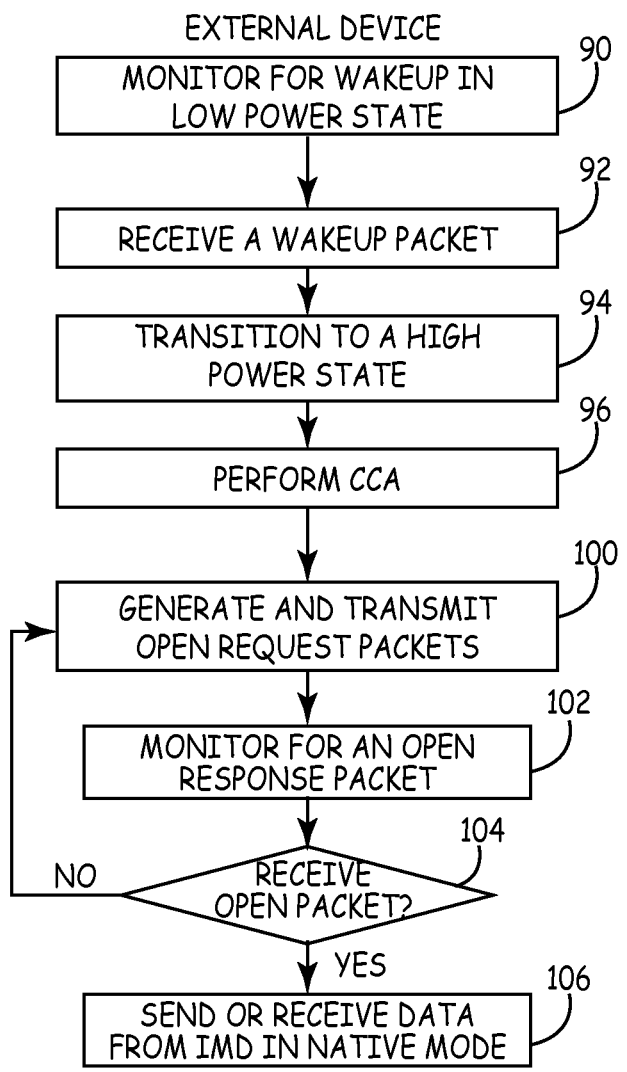
FIG. 7 is a flow diagram illustrating example operation of a telemetry module of an external device establishing a communication session in accordance with another embodiment of this disclosure.

FIG. 7 is a flow diagram illustrating example operation of telemetry module 22 of an external device 18 in accordance with another embodiment of this disclosure. Telemetry module 22 may, for example, operate in accordance with the flow diagram of FIG. 7 to establish a communication session with an IMD 14 that is operating in accordance with the flow diagram of FIG. 6. The flow diagram of FIG. 7 conforms substantially to the flow diagram of FIG. 5 except the step described with respect to block 98 is not performed. Instead, telemetry module 38 of external device 18 immediately begins to transmit open request packets (e.g., native mode communications) in the high power state without sending any wakeup packets.

Figure 8:
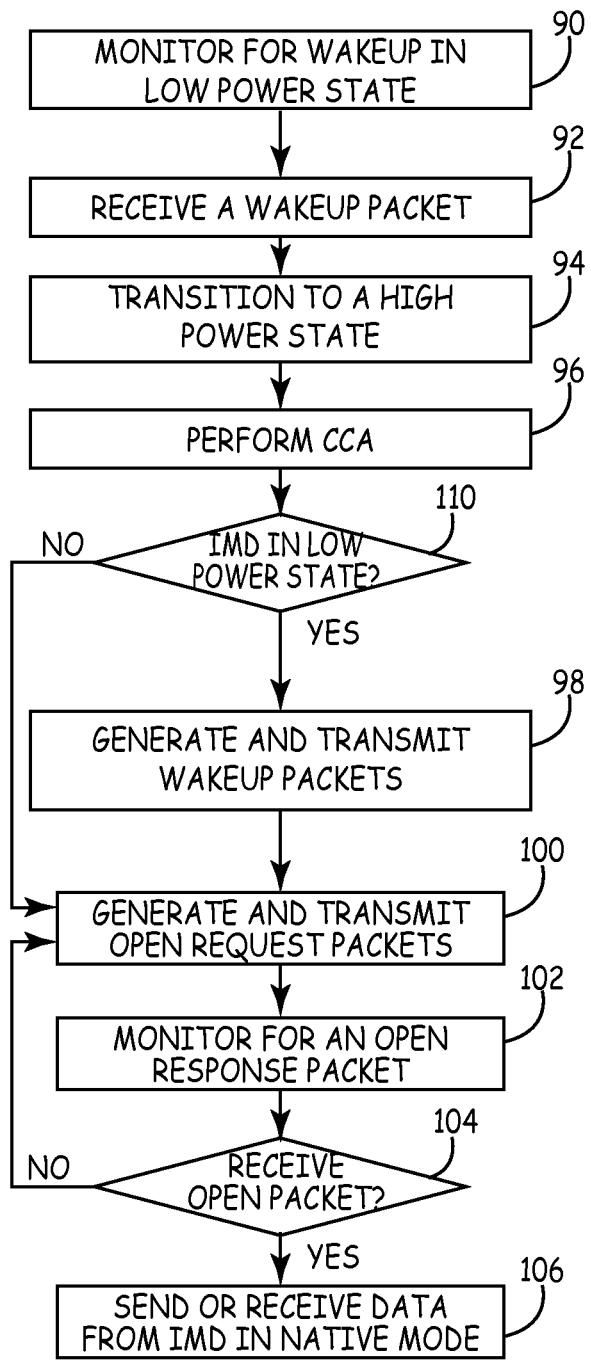
FIG. 8 is another flow diagram illustrating example operation of a telemetry module of an external device in accordance with a further embodiment of this disclosure.

FIG. 8 is another flow diagram illustrating example operation of telemetry module 22 of an external device 18 in accordance with a further embodiment of this disclosure. The flow diagram of FIG. 8 conforms substantially to the flow diagram of FIG. 5 except telemetry module 22 determines whether IMD is operating in a low power state to determine which type of communications to transmit to IMD 14 (110). In one example, the wakeup packet from telemetry module 38 of IMD 14 may specify the amount of time that IMD 14 will operate in the high power state before reverting back to the low power state. External device 18 may determine whether telemetry module is operating in the low power state based on the information in the wakeup packet.

When external device 18 determines that telemetry module 38 of IMD 14 is operating in the low power state (e.g., when the amount of time specified in the wakeup packet has elapsed) ("YES" branch of block 110), telemetry module 22 of external device 18 transmits one or more wakeup packets to IMD 14 (98) followed by one or more open request packets (100). When external device 18 determines that telemetry module 38 of IMD 14 is operating in the high power state (e.g., when the amount of time specified in the wakeup packet has not elapsed) ("NO" branch of block 110), telemetry module 22 of external device 18 transmits one or more open request packets on the selected channel without sending any wakeup packets (100). The remaining steps correspond to the like numbered steps described in detail in FIG. 5 and will not be repeated here.

The techniques described in this disclosure may be implemented, at least in part, in hardware, software, firmware or any combination thereof For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, SRAM, NVRAM, EEPROM, FLASH memory, magnetic data storage media, optical data storage media, or the like. The instructions may be executed to support one or more aspects of the functionality described in this disclosure. Various examples have been described. These and other examples are within the scope of the following claims.

The invention claimed is:

1. A method of communicating between an external device and an implantable medical device, the method comprising:
    operating a telemetry module of the external device in a low power state in which the telemetry module interleaves intervals during which one or more components of the telemetry module are powered down with intervals during which the one or more components of the telemetry module are powered up;
    receiving, by the external device, a wakeup communication from the implantable medical device;
    transitioning the telemetry module of the external device from the low power state to a high power state in response to receiving the wakeup communication from the implantable medical device;
    transmitting one or more communications from the external device to the implantable medical device to establish a communication session in response to transitioning to the high power state, wherein transmitting the one or more communications comprises:
        transmitting, with the external device, at least one wakeup communication to the implantable medical device in a first communication mode; and
        transmitting, with the external device, at least one packet to the implantable medical device in a second communication mode indicating a desire to open the communication session subsequent to the at least one wakeup communication.

2. The method of claim 1, wherein transitioning the telemetry module from the low power state to the high power state comprises transitioning the telemetry module to a high power state in which the one or more components of the telemetry module remain powered up.

3. The method of claim 1, wherein transitioning the telemetry module from the low power state to the high power state comprises transitioning the telemetry module to a high power state in which the one or more components of the telemetry module are powered up with a different duty cycle than the low power state, wherein the one or more components are powered up more often in the high power state than in the low power state.

4. The method of claim 1, wherein the first communication mode includes at least one of an encoding scheme, a data rate, a packet size, a packet structure, and a frequency that is different from the second communication mode.

5. The method of claim 1, further comprising powering the receiver of the device using a battery, wherein the low power state extends a service life of the battery.

6. The method of claim 1, further comprising:
    measuring ambient power levels on at least a portion of a plurality of channels of a frequency band in response to the wakeup communication from the implantable medical device; and
    selecting, with the external device, one of the plurality of channels having a low measured ambient power level for transmitting communications to the implantable medical device; and
    wherein transmitting one or more communications from the external device to the implantable medical device further comprises transmitting the one or more communications on the selected communication channel.

7. The method of claim 6, wherein selecting one of the plurality of channels having a low measured ambient power level for transmitting communications to the implantable medical device comprises selecting, with the external device, the one of the plurality of channels of the frequency band having the lowest measured ambient power level.

8. The method of claim 6, wherein selecting one of the plurality of channels having a low measured ambient power level for transmitting communications to the implantable medical device comprises selecting, with the external device, one of the plurality of channels of the frequency band having an ambient power level below a minimum power level threshold.

9. An external device for communicating with an implantable medical device, the external device comprising:
    an antenna to transmit or receive communications from the implantable medical device; and
    a telemetry module coupled to the antenna, the telemetry module configured to operate in a low power state in which the telemetry module interleaves intervals during which one or more components of the telemetry module are powered down with intervals during which the one or more components of the telemetry module are powered up, receive a wakeup communication from the implantable medical device, transition from the low power state to a high power state in response to receiving the wakeup communication, and transmit one or more communications to the implantable medical device to establish a communication session in response to transitioning to the high power state, wherein the telemetry module transmits, to the implantable medical device, at least one wakeup communication in a first communication mode and transmits, to the implantable medical device, at least one packet in a second communication mode indicating a desire to open the communication session subsequent to the at least one wakeup communication.

10. The device of claim 9, wherein the telemetry module transitions from the low power state to a high power state in which the one or more components of the telemetry module remain powered up.

11. The device of claim 9, wherein the telemetry module transitions from the low power state to a high power state in which the one or more components of the telemetry module are powered up with a different duty cycle than the low power state, wherein the one or more components are powered up more often in the high power state than in the low power state.

12. The device of claim 9, wherein the first communication mode includes at least one of an encoding scheme, a data rate, a packet size, a packet structure, and a frequency that is different from the second communication mode.

13. The device of claim 9, further comprising a power supply for powering the components of the device, wherein the low power state extends a service life of the power supply.

14. The device of claim 13, wherein the power supply comprises one of a rechargeable battery and a non-rechargeable battery.

15. The device of claim 9, wherein the telemetry module is further configured to measure ambient power levels on at least a portion of a plurality of channels of a frequency band in response to the wakeup communication from the implantable medical device, select one of the plurality of channels having a low measured ambient power level for transmitting communications to the implantable medical device, and transmit the one or more communications to the implantable medical device over the selected communication channel.

16. The device of claim 15, wherein the telemetry module of the external device is configured to select the one of the plurality of channels of the frequency band having the lowest measured ambient power level.

17. The device of claim 15, wherein the telemetry module of the external device is configured to select one of the plurality of channels of the frequency band having a measured ambient power level below a minimum power level threshold.

\* \* \* \* \*